United States Patent
Yapp et al.

(10) Patent No.: US 12,224,065 B2
(45) Date of Patent: Feb. 11, 2025

(54) AUGMENTING FILES SUCH AS DICOM OBJECTS CONTAINING MEDICAL IMAGING INFORMATION WITH ADDITIONAL MEDICAL INFORMATION ABOUT THE SUBJECT OF THE MEDICAL IMAGING INFORMATION

(71) Applicant: Providence St. Joseph Health, Seattle, WA (US)

(72) Inventors: Lawrence Frederick Yapp, Auburn, WA (US); Janet Marie Vickers, Bothell, WA (US); Jennifer Grace Franks, Puyallup, WA (US)

(73) Assignee: Providence St. Joseph Health, Seattle, WA (US)

( * ) Notice: Subject to any disclaimer, the term of this patent is extended or adjusted under 35 U.S.C. 154(b) by 307 days.

(21) Appl. No.: 17/940,628

(22) Filed: Sep. 8, 2022

(65) Prior Publication Data

US 2024/0087740 A1    Mar. 14, 2024

(51) Int. Cl.
  *G16H 50/20*    (2018.01)
  *G16H 10/60*    (2018.01)
  *G16H 30/20*    (2018.01)
  *G16H 30/40*    (2018.01)

(52) U.S. Cl.
  CPC ............ *G16H 50/20* (2018.01); *G16H 10/60* (2018.01); *G16H 30/20* (2018.01); *G16H 30/40* (2018.01)

(58) Field of Classification Search
  None
  See application file for complete search history.

(56) References Cited

U.S. PATENT DOCUMENTS

| | | | |
|---|---|---|---|
| 2006/0242148 A1* | 10/2006 | Rothpearl | G16H 30/20 |
| 2020/0035363 A1* | 1/2020 | Vogt | G16H 30/40 |
| 2020/0303060 A1* | 9/2020 | Haemel | G06N 3/082 |
| 2021/0343395 A1* | 11/2021 | Pan | G16H 30/20 |

OTHER PUBLICATIONS

Graham et al. ("DICOM demystified: a review of digital file formats and their use in radiological practice." Clinical radiology 60.11 (2005): 1133-1140) (Year: 2005).*
Huang et al., "Fusion of Medical Imaging and Electronic Health Records Using Deep Learning: a Systematic Review and Implementation Guidelines," *Nature Journal NPL Digital Medicine* 3(136): 1-9, Oct. 2020.
International Search Report and Written Opinion, mailed Dec. 4, 2023, for Application No. PCT/US2023/030281. (11 pages).
Pérez et al., "An Automatic Method for the Enrichment of DICOM Metadata Using Biomedical Ontologies," *37th Annual International Conference of the IEEE Engineering in Medicine and Biology Society (EMBC)*, Milan, Italy, Aug. 25-29, 2015, pp. 2551-2554.

* cited by examiner

*Primary Examiner* — Christopher B Tokarczyk
(74) *Attorney, Agent, or Firm* — Seed Intellectual Property Law Group LLP (57) ABSTRACT

A facility for performing an enrichment process is disclosed. The facility accesses a starting file emitted by a medical imaging device, which contains (1) medical imaging information captured from a subject, and information identifying the subject. The facility uses the information identifying the subject in the starting file to extract medical information from an electronic medical record corresponding to the subject. The facility then creates an enriched file by making a copy of the starting file and adding the extracted medical information to the copy.

9 Claims, 6 Drawing Sheets

| Tag | Name | Value |
|---|---|---|
| (0x0008, 0x1030) | Study Description | 'CT_ABDOMEN_W_IV_CONTRAST' |
| (0x0008, 0x103e) | Series Description | 'ABD' |
| (0x0010, 0x0010) | Patient's Name | 'SIMPSON_HOMER_J' |
| (0x0010, 0x0020) | Patient ID ("MRN") | '5553226' |
| (0x0020, 0x000d) | Study Instance UID | 1.2.826.0.1.3680043.2.1125.1.38381854871216336385978062044218957 |
| (0x0020, 0x000e) | Series Instance UID | 1.2.826.0.1.3680043.2.1125.1.6887895998483772644791670755139966 |
| (0x0020, 0x0013) | Instance Number | "20" |
| (0x7fe0, 0x0010) | Pixel Data | Array of 524288 elements |

Enriched DICOM object

| | Tag | Name | Value |
|---|---|---|---|
| 501 | (0x0008, 0x1030) | Study Description | 'CT_ABDOMEN_W_IV_CONTRAST' |
| 502 | (0x0008, 0x103e) | Series Description | 'ABD' |
| 503 | (0x0010, 0x0010) | Patient's Name | 'SIMPSON_HOMER_J' |
| 504 | (0x0010, 0x0020) | Patient ID ("MRN") | '5553226' |
| 505 | (0x0020, 0x000d) | Study Instance UID | 1.2.826.0.1.3680043.2.1125.1.38381854871216336385978062044218957 |
| 506 | (0x0020, 0x000e) | Study Instance UID | 1.2.826.0.1.3680043.2.1125.1.68878959984837726447916707551399667 |
| 507 | (0x0020, 0x0013) | Instance Number | '20' |
| 508 | (0x7fe0, 0x0010) | Pixel Data | Array of 524288 elements |
| 511 | (0x3010, 0x007f) | Fractionation Notes | "My notes: This is how value was calculated based on...." |
| 521 | (0x3001, 0x0001) | | PR:DB3/STG3/PROBLEM1/ReasonForVisit=Abdominal pain |
| 522 | (0x3001, 0x0002) | | PR:DB3/STG3/PROBLEM2/BMI=27.3 |
| 523 | (0x3001, 0x0003) | | PR:DB3/STG3/PROBLEM3/BUN=8 mg/dl |
| 524 | (0x3001, 0x0004) | | PR:DB3/STG3/PROBLEM4/GFR=60 |
| 525 | (0x3001, 0x0005) | | PR:DB3/STG3/PROBLEM5/HistoryOfDiabetes=Yes |
| 526 | (0x3001, 0x0006) | | PR:DB3/STG3/PROBLEM6/HistoryOfHypertension=Yes |
| 527 | (0x3001, 0x0007) | | PR:DB3/STG3/PROBLEM7/HistoryOfKidneyDisease=No |

FIG. 6

AUGMENTING FILES SUCH AS DICOM OBJECTS CONTAINING MEDICAL IMAGING INFORMATION WITH ADDITIONAL MEDICAL INFORMATION ABOUT THE SUBJECT OF THE MEDICAL IMAGING INFORMATION

BACKGROUND

It is common to perform machine learning on the basis of visual information such as still images and video sequences produced by various medical imaging modalities, such as x-ray, ultrasound ("US"), angiography, magnetic resonance imaging ("MRI"), computed tomography ("CT"), positron emission tomography ("PET"), and single-photon emission computed tomography ("SPECT").

Some medical imaging machines store the raw data making up the visual information artifacts they produce in data objects called DICOM objects. In some cases, when creating DICOM objects, medical imaging machines include metadata in addition to the artifact raw data, such as the type of machine that produced the artifact, the machine configuration settings used to produce the artifact, the dimensions of the artifact, the frame rate of a video artifact, etc. NEMA PS3/ISO 12052, Digital Imaging and Communications in Medicine (DICOM) Standard, National Electrical Manufacturers Association, Rosslyn, VA, USA (available free at www.dicomstandard.org/) specifies the composition of DICOM objects, and is incorporated by reference in its entirety. In cases where a document incorporated herein by reference conflicts with the present disclosure, the present disclosure controls.

It is common to perform machine learning on the basis of visual information produced by medical imaging. To do so, it is typical to train a neural network or other machine learning model using training observations each corresponding to a different subject. Each training observation has as an independent variable visual data captured from the subject using medical imaging, and has a dependent variable constituting some conclusion formed from that visual data, such as the diagnosis of a medical condition based on the visual data. The trained model can then be applied to medical imaging visual data captured from a patient to predict the dependent variable conclusion for the patient, such as diagnosis.

DETAILED DESCRIPTION

The inventors have recognized that, in performing machine learning on visual information produced by medical imaging, the quality of prediction results can be improved by including additional independent variables in each training observation and prediction request, including such information about the subjects as age, sex, height, weight, BMI, prescriptions, surgical procedures, test results, medical complaints, medical diagnoses, etc.

The inventors have further recognized that it can be difficult for the designers and implementers of machine learning projects that seek to include this additional medical information about subjects along with their medical imaging information to obtain the additional medical information for the correct subjects and correctly correlate it with the medical imaging information from each subject. In particular, for medical imaging information, HIPAA or other medical privacy laws and rules may prohibit including with medical imaging information used in this way the kind of subject identity information that would be needed to obtain and correlate the subject's additional medical information. Even where such correlation proves to be possible, though, it remains error-prone, laborious, and potentially incomplete.

In response to these observations, the inventors have conceived and reduced to practice a software and/or hardware facility for augmenting, or "enriching," files such as DICOM objects containing medical imaging information with additional medical information about the subject of the medical imaging information ("the facility").

In some embodiments, the facility supports the creation of a DICOM enrichment template that specifies a particular way of enriching DICOM objects. In particular, the enrichment template specifies one or more fields, or "tags," to be added to each DICOM object to which it is applied. For each of these added fields, the template includes two kinds of data: (1) a name or location usable to locate the field's value in the DICOM object, such as a field name, a tag name, or an offset from the beginning of the DICOM object; and (2) a way to retrieve the field's value for the subject for population into the enriched DICOM object, such as a table and column in a database maintained by Electronic Medical Record software ("EMR" or "EHR") for which the corresponding value is stored for each person having a record in the EMR. As one example, for a HistoryOfDiabetes field, a template may contain (1) the field name "(0x3001, 0x0005)" in the DICOM format of (<group number>, <element number>), and (2) the EMR path "DB3/STG3/PROBLEM5/HistoryOfDiabetes"—made up of EMR database name "DB3", the schema "STG3", the table "PROBLEM5", and the column "HistoryOfDiabetes"—usable to retrieve the value of this field for any person having a record in the EMR. For any subject for which a DICOM object is produced to contain medical imaging information from the subject, the contents of the template can be used to retrieve values of the enrichment fields specified by the template for the subject, and store them in the DICOM object. In some embodiments, the template can also specify the removal, or full or partial anonymization of original fields of the DICOM object that contain identifying information for the subject, such as name, social security number, patient identifier, etc.

In some embodiments, the creator of a machine learning project or a collaborator specifies three pieces of information in order to obtain a set of enriched DICOM objects: (1) a subject criteria query specifying EMR attributes of subjects who qualify to be included in the project; (2) information identifying the DICOM object that is to be extracted from the EMR for each qualifying subject; and (3) information identifying a template that is to be used to enrich each of the extracted DICOM objects with additional medical information of its subject. For example, the creator of a particular project could specify (1) a query selecting females of age 28-42 with a BMI 29-37, a positive or negative hypertension diagnosis, and a cardiac ultrasound captured between 20210901 and 20220831; (2) a request to extract the most recent cardiac ultrasound 20210901 and 20220831; and (3) the sample template described above. In response, the facility selects a group of subjects who satisfy the query; extracts the appropriate ultrasound DICOM object for each; and enriches these extracted DICOM objects in accordance with the identified template. The enriched DICOM objects are then each used as a training observation to train a machine learning model, identifying the positive or negative hypertension diagnosis as the dependent variable of the training observation, and the medical imaging information and other enrichment fields as independent variables.

To apply a machine learning model trained using enriched DICOM objects, in some embodiments the facility monitors a feed of DICOM objects being stored in the EMR, and applies the query that is the basis for the project to the EMR records in which they are being stored (except any portion of the query that relates to the dependent variable, such as hypertension diagnosis in the above example). For matching records, the facility extracts the DICOM object, and enriches it in accordance with the template identified for the project (again, except for enrichment fields that relate to the model's dependent variable). The facility then applies the trained machine learning model to this enriched DICOM object to produce an inference about the independent variable for the person. This inference can be stored in the person's EMR record, sent to the person's caregiver, etc.

In some embodiments, the facility enriches DICOM objects in the way described above to serve as standalone resources for radiologists and other imaging interpretation specialists to review the contained imaging information without the need to access the patient's EMR record for additional medical information contained there that is relevant to making an accurate assessment of the imaging information. This can make it possible for such imaging readers to operate in a variety of locations and conditions, without requiring a live, secure connection to the EMR containing the patient's other medical information, leveraging encryption and/or other data protection schemes already applied to unenriched DICOM objects.

By operating in some or all of the ways described above, the facility makes it easy and fast for the creator of a machine learning project based on medical imaging information to obtain high-quality training data for the project that contains a tailored set of medical information about each subject; protects subject confidentiality; and/or enables radiologists and other readers of medical imaging information to receive patient information needed to perform an assessment in the same data object as the medical imaging information eliminating the need for a live, secure EMR connection, as well as the need to navigate the EMR user interface to access the patient information inside the EMR.

Additionally, the facility improves the functioning of computer or other hardware, such as by reducing the dynamic display area, processing, storage, and/or data transmission resources needed to perform a certain task, thereby enabling the task to be permitted by less capable, capacious, and/or expensive hardware devices, and/or be performed with lesser latency, and/or preserving more of the conserved resources for use in performing other tasks. For example, by automatically extracting and enriching DICOM files, the facility eliminates the processing, storage, and data transmission resources that would be needed to support manual efforts to produce the same results. Also, by allowing the tailoring of subject selection and independent variables used, the facility makes it more likely that models will produce useful results, and thus the processing, storage, and transmission resources needed to train replacement models will be reduced. Further, by encapsulating patient medical information needed to read medical image information, the facility eliminates the need for any hardware resources needed to maintain a live, secure connection to the EMR where this medical information is hosted.

Figure 1:
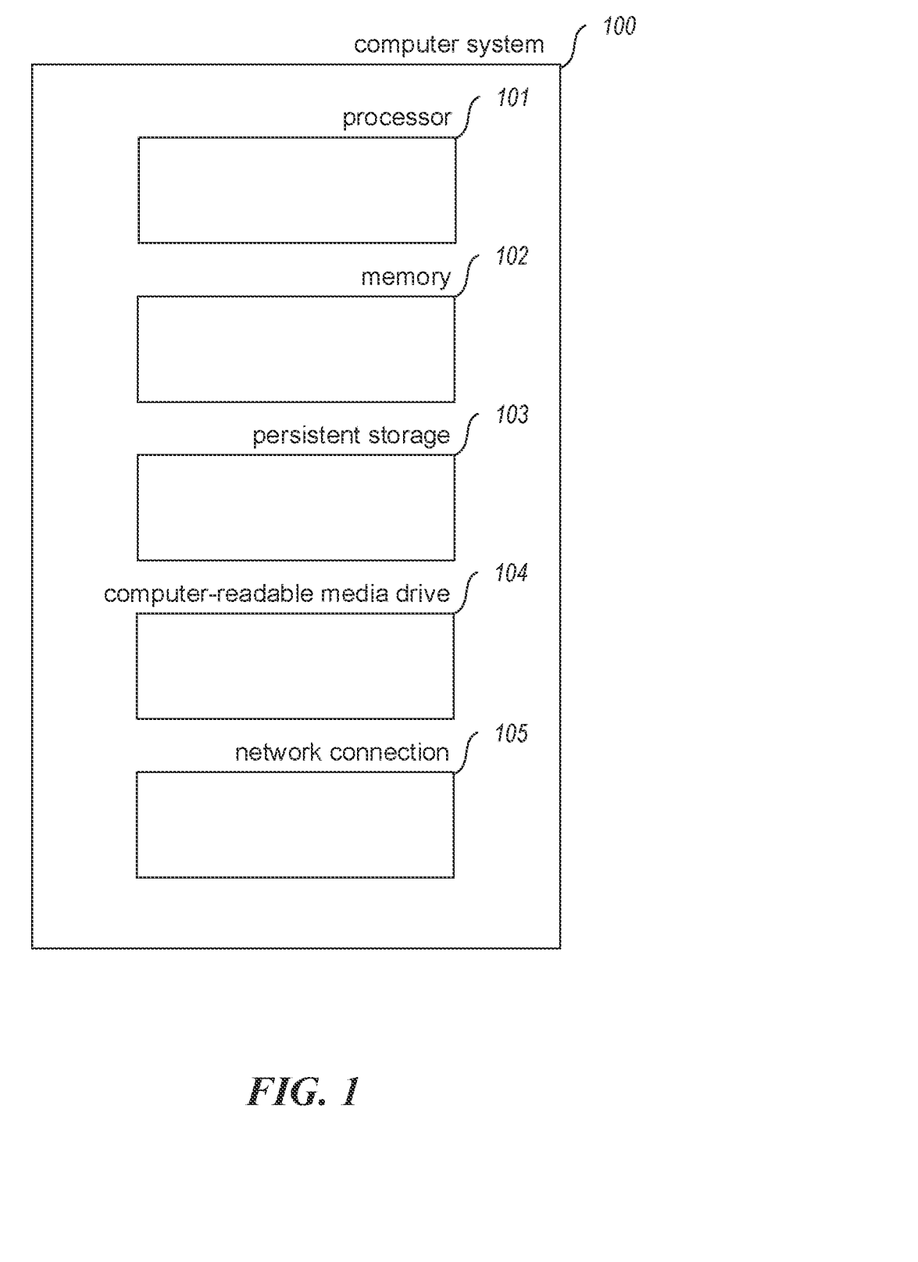
FIG. 1 is a block diagram showing some of the components typically incorporated in at least some of the computer systems and other devices on which the facility operates.

FIG. 1 is a block diagram showing some of the components typically incorporated in at least some of the computer systems and other devices on which the facility operates. In various embodiments, these computer systems and other devices 100 can include server computer systems, cloud computing platforms or virtual machines in other configurations, desktop computer systems, laptop computer systems, netbooks, mobile phones, personal digital assistants, televisions, cameras, automobile computers, electronic media players, etc. In various embodiments, the computer systems and devices include zero or more of each of the following: a processor 101 for executing computer programs and/or training or applying machine learning models, such as a CPU, GPU, TPU, NNP, FPGA, or ASIC; a computer memory 102 for storing programs and data while they are being used, including the facility and associated data, an operating system including a kernel, and device drivers; a persistent storage device 103, such as a hard drive or flash drive for persistently storing programs and data; a computer-readable media drive 104, such as a floppy, CD-ROM, or DVD drive, for reading programs and data stored on a computer-readable medium; and a network connection 105 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

Figure 2:
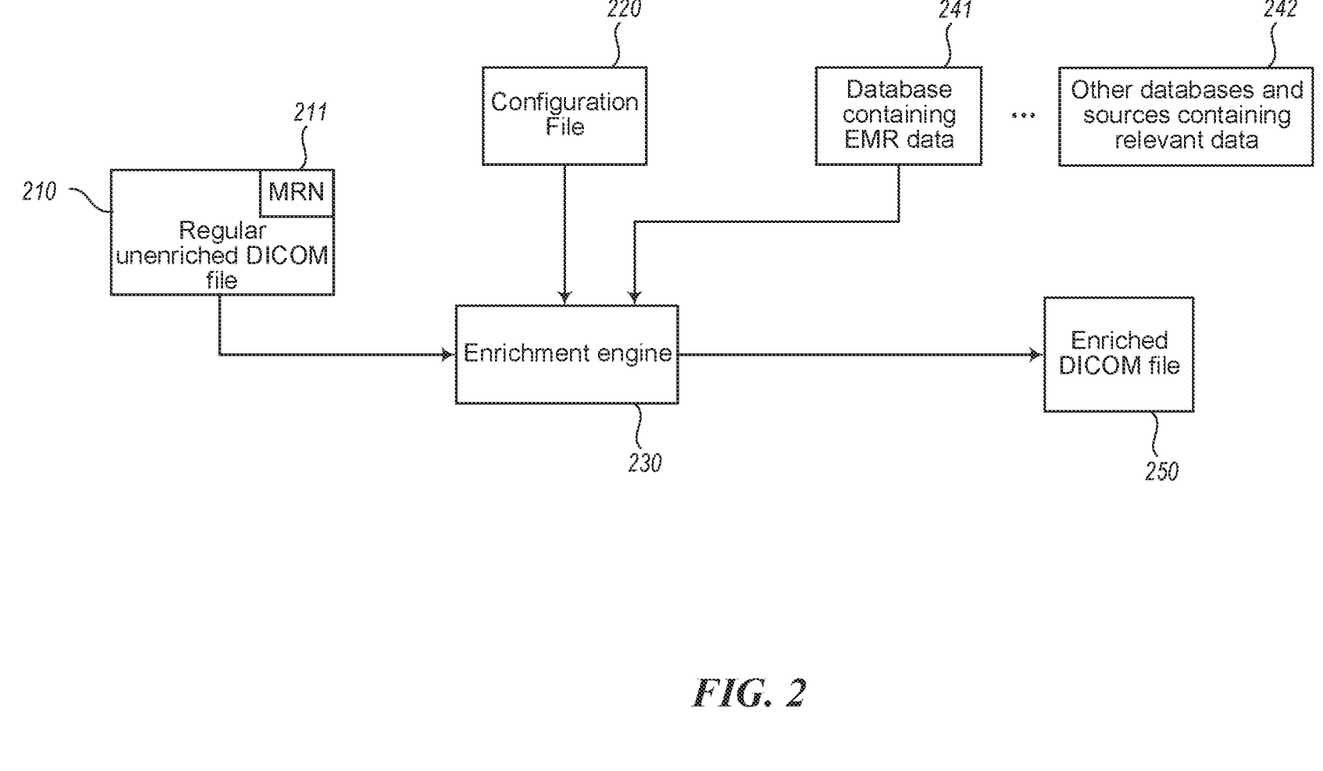
FIG. 2 is a data flow diagram depicting the operation of the facility in some embodiments.

FIG. 2 is a data flow diagram depicting the operation of the facility in some embodiments. A DICOM file 210 is emitted by a medical imaging device, and contains one or more medical imaging artifacts of a subject. These may be one or more still images, a video sequence, one or more 3D images, a 3D video sequence, etc. The DICOM file also includes an identifier identifying the subject of the artifacts. For example, in some embodiments, the DICOM file includes a medical record number, or "MRN," used by some EMRs to identify the people for whom they store medical information. The facility establishes a workflow that routes some or all DICOM files to an enrichment engine 230. The enrichment engine consults a configuration file 220, which specifies how the DICOM file is to be enriched using additional information about the subject of the artifacts contained by the DICOM file. In particular, for each of one or more information fields to be added, configuration file specifies (1) how to use the subject's identifying information to retrieve data for populating into the additional field from a database 241 containing EMR data—such as one maintained by the EMR—and/or other databases and sources 242 containing relevant data; and (2) a place to store this retrieved information in an enriched version of the DICOM file. The enrichment engine uses this direction from a configuration file in order to retrieve the additional information about the subject, and store it in a copy of the DICOM file. This copy is referred to as an "enriched DICOM file."

Figure 3:
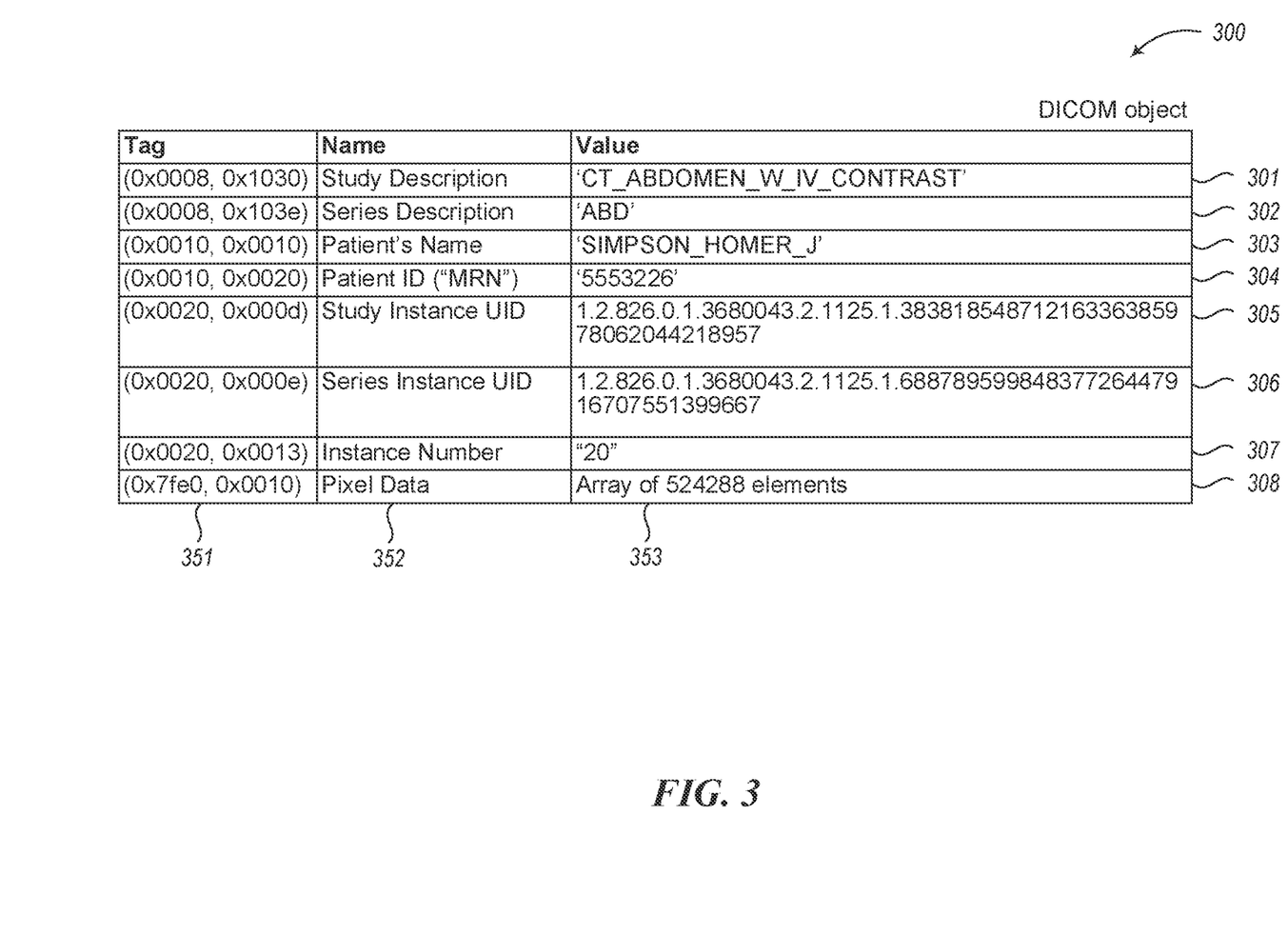
FIG. 3 is a table diagram showing sample contents of a starting DICOM object that can be enriched by the facility in some embodiments.

FIG. 3 is a table diagram showing sample contents of a starting DICOM object that can be enriched by the facility in some embodiments. As shown, the DICOM object is made up of rows—also called fields, elements, or tags—such as rows 301-308. As shown, each row is divided into the following columns: a tag identifier column 351, uniquely identifying the row; a name column 352 giving a description of the value stored in the field; and a value column 353 containing the value stored in the field. For example, row 301 indicates that the Study Description field (0x0008, 0x1030) has the value 'CT_ABDOMEN_W_IV_CONTRAST'. Row 304 indicates that the Patient ID field (i.e., the MRN field), (0x0010, 0x0020), has the value '5553226'. Further, row 308 contains the raw data making up the medical imaging artifact in Pixel Data field (0x7fe0, 0x0010).

While FIG. 3 and each of the table diagrams discussed below show a table whose contents and organization are designed to make them more comprehensible by a human reader, those skilled in the art will appreciate that actual data structures used by the facility to store this information may differ from the table shown, in that they, for example, may be organized in a different manner; may contain more or less information than shown; may be compressed, encrypted, and/or indexed; may contain a much larger number of rows than shown, etc.

Figure 4:
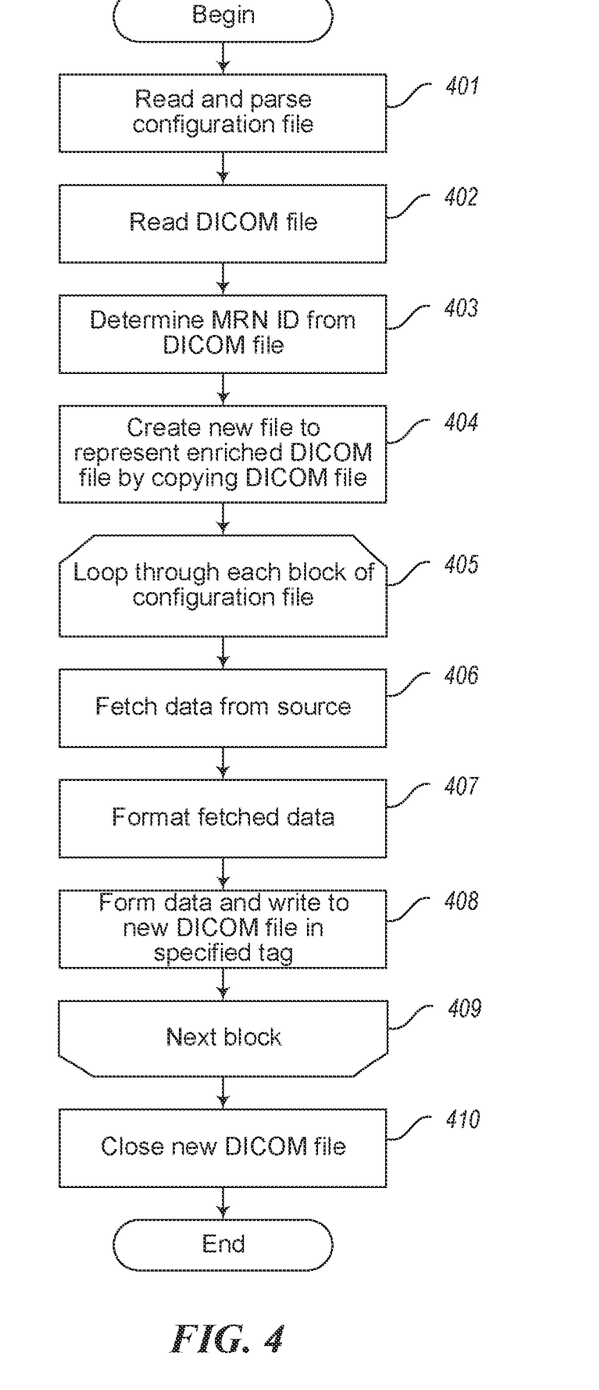
FIG. 4 is a flow diagram showing a process performed by the facility in some embodiments in order to enrich a DICOM object.

FIG. 4 is a flow diagram showing a process performed by the facility in some embodiments in order to enrich a DICOM object. In act 401, the facility reads and parses a configuration file. In some embodiments, the facility maintains multiple configuration files, each for a different enrichment project. In such embodiments, the facility selects the appropriate configuration file for the project to which the DICOM object to be enriched belongs. Table 1 below shows a sample configuration file used by the facility in some embodiments.

TABLE 1

| 1  | <dicom-tag-mappings> |
| --- | --- |
| 2  |   <dicom-tag-mapping> |
| 3  |     <dicom-tag> |
| 4  |       <type>Inbuilt</type> |
| 5  |       <tag>FractionationNotes</tag> |
| 6  |     </dicom-tag> |
| 7  |     <source> |
| 8  |       <database>DB1</database> |
| 9  |       <schema>STG1</schema> |
| 10 |       <table>PROBLEM1</table> |
| 11 |       <column>FractionationNotes</column> |
| 12 |     </source> |
| 13 |   </dicom-tag-mapping> |
| 14 |   <dicom-tag-mapping> |
| 15 |     <dicom-tag> |
| 16 |       <type>Custom</type> |
| 17 |       <tag>0x3001, 0x0001</tag> |
| 18 |     </dicom-tag> |
| 19 |     <source> |

TABLE 1-continued

| 20 |       <database>DB3</database> |
| --- | --- |
| 21 |       <schema>STG3</schema> |
| 22 |       <table>PROBLEM1</table> |
| 23 |       <column>ReasonForVisit</column> |
| 24 |     </source> |
| 25 |   </dicom-tag-mapping> |
| 26 |   <dicom-tag-mapping> |
| 27 |     <dicom-tag> |
| 28 |       <type>Custom</type> |
| 29 |       <tag>0x3001, 0x0002</tag> |
| 30 |     </dicom-tag> |
| 31 |     <source> |
| 32 |       <database>DB3</database> |
| 33 |       <schema>STG3</schema> |
| 34 |       <table>PROBLEM2</table> |
| 35 |       <column>BMI</column> |
| 36 |     </source> |
| 37 |   </dicom-tag-mapping> |
| 38 |   <dicom-tag-mapping> |
| 39 |     <dicom-tag> |
| 40 |       <type>Custom</type> |
| 41 |       <tag>0x3001, 0x0003</tag> |
| 42 |     </dicom-tag> |
| 43 |     <source> |
| 44 |       <database>DB3</database> |
| 45 |       <schema>STG3</schema> |
| 46 |       <table>PROBLEM3</table> |
| 47 |       <column>BUN</column> |
| 48 |     </source> |
| 49 |   </dicom-tag-mapping> |
| 50 |   <dicom-tag-mapping> |
| 51 |     <dicom-tag> |
| 52 |       <type>Custom</type> |
| 53 |       <tag>0x3001, 0x0004</tag> |
| 54 |     </dicom-tag> |
| 55 |     <source> |
| 56 |       <database>DB3</database> |
| 57 |       <schema>STG3</schema> |
| 58 |       <table>PROBLEM4</table> |
| 59 |       <column>GFR</column> |
| 60 |     </source> |
| 61 |   </dicom-tag-mapping> |
| 62 |   <dicom-tag-mapping> |
| 63 |     <dicom-tag> |
| 64 |       <type>Custom</type> |
| 65 |       <tag>0x3001, 0x0005</tag> |
| 66 |     </dicom-tag> |
| 67 |     <source> |
| 68 |       <database>DB3</database> |
| 69 |       <schema>STG3</schema> |
| 70 |       <table>PROBLEM5</table> |
| 71 |       <column>HistoryOfDiabetes</column> |
| 72 |     </source> |
| 73 |   </dicom-tag-mapping> |
| 74 |   <dicom-tag-mapping> |
| 75 |     <dicom-tag> |
| 76 |       <type>Custom</type> |
| 77 |       <tag>0x3001, 0x0006</tag> |
| 78 |     </dicom-tag> |
| 79 |     <source> |
| 80 |       <database>DB3</database> |
| 81 |       <schema>STG3</schema> |
| 82 |       <table>PROBLEM6</table> |
| 83 |       <column>HistoryOfHypertension</column> |
| 84 |     </source> |
| 85 |   </dicom-tag-mapping> |
| 86 |   <dicom-tag-mapping> |
| 87 |     <dicom-tag> |
| 88 |       <type>Custom</type> |
| 89 |       <tag>0x3001, 0x0007</tag> |
| 90 |     </dicom-tag> |
| 91 |     <source> |
| 92 |       <database>DB3</database> |
| 93 |       <schema>STG3</schema> |
| 94 |       <table>PROBLEM7</table> |
| 95 |       <column>HistoryOfKidneyDisease</column> |
| 96 |     </source> |
| 97 |   </dicom-tag-mapping> |
| 98 | </dicom-tag-mappings> |

In act 402, the facility reads the DICOM file. In act 403, the facility identifies the MRN ID or other patient or subject identifier contained by the DICOM file. In some embodiments, for example, this involves reading an MRN or other patient ID from a field like the one shown in row 304 of FIG. 3. In act 404, the facility creates a new file to represent the enriched DICOM file by copying the DICOM file read in act 402. In some embodiments, in creating this new file, the facility omits certain information from the DICOM file, such as information that tends to identify the subject, which may include the subject's MRN or other identifier; name; postal address, etc. In acts 405-409, the facility loops through each of a number of blocks of the configuration file, each of which corresponds to a different additional field to include in the enriched DICOM file. The sample configuration file shown in Table 1 contains eight blocks, each corresponding to a different additional field: a first block shown in lines 2-13, a second block shown in lines 14-25, a third block shown in lines 26-37, a fourth block shown in lines 38-49, a fifth block shown in lines 50-61, a sixth block shown in lines 62-73, a seventh block shown in lines 74-85, and an eighth block shown in lines 86-97. In act 406, the facility fetches data about the subject from a data source in accordance with the retrieval information contained in the current block. For example, the first block of the configuration file in lines 2-13 specifies retrieving a value for the FractionationNotes field from the FractionationNotes column of the subject's row of the PROBLEM1 table in the STG1 schema of the DB1 database. Similarly, the second block in lines 14-25 specifies retrieving a value for the custom ReasonForVisit field from the ReasonForVisit column of the subject's row of the PROBLEM1 table in the STG3 schema of the DB3 database.

In act 407, the facility formats the fetched data. In various embodiments, this formatting is performed in a way that is standard across all field types, in a way that is standard per field type, in a way that can be overridden by the configuration file, such as in the block corresponding to the field, etc. In act 408, the facility forms the data and writes it to the new DICOM file in the tag specified by the configuration file block. For example, for the first block, the facility writes the retrieved value for the FractionationNotes field to an inbuilt FractionationNotes tag specified by the DICOM standard, to be at the tag ID (0x3010, 0x007f). For the second block, the facility stores the value retrieved for the ReasonForVisit field to a custom tag not specified by the DICOM standard having tag ID (0x3001, 0x0001). In act 409, if additional blocks of the configuration file remain to be processed, then the facility continues in act 405 to process the next block, else the facility continues in act 410. In act 410, the facility closes the new DICOM file, and identifies it as the enriched version of the DICOM file read in act 402. After act 410, this process concludes.

Those skilled in the art will appreciate that the acts shown in FIG. 4 and in each of the flow diagrams discussed below may be altered in a variety of ways. For example, the order of the acts may be rearranged; some acts may be performed in parallel; shown acts may be omitted, or other acts may be included; a shown act may be divided into subacts, or multiple shown acts may be combined into a single act, etc.

Figure 5:
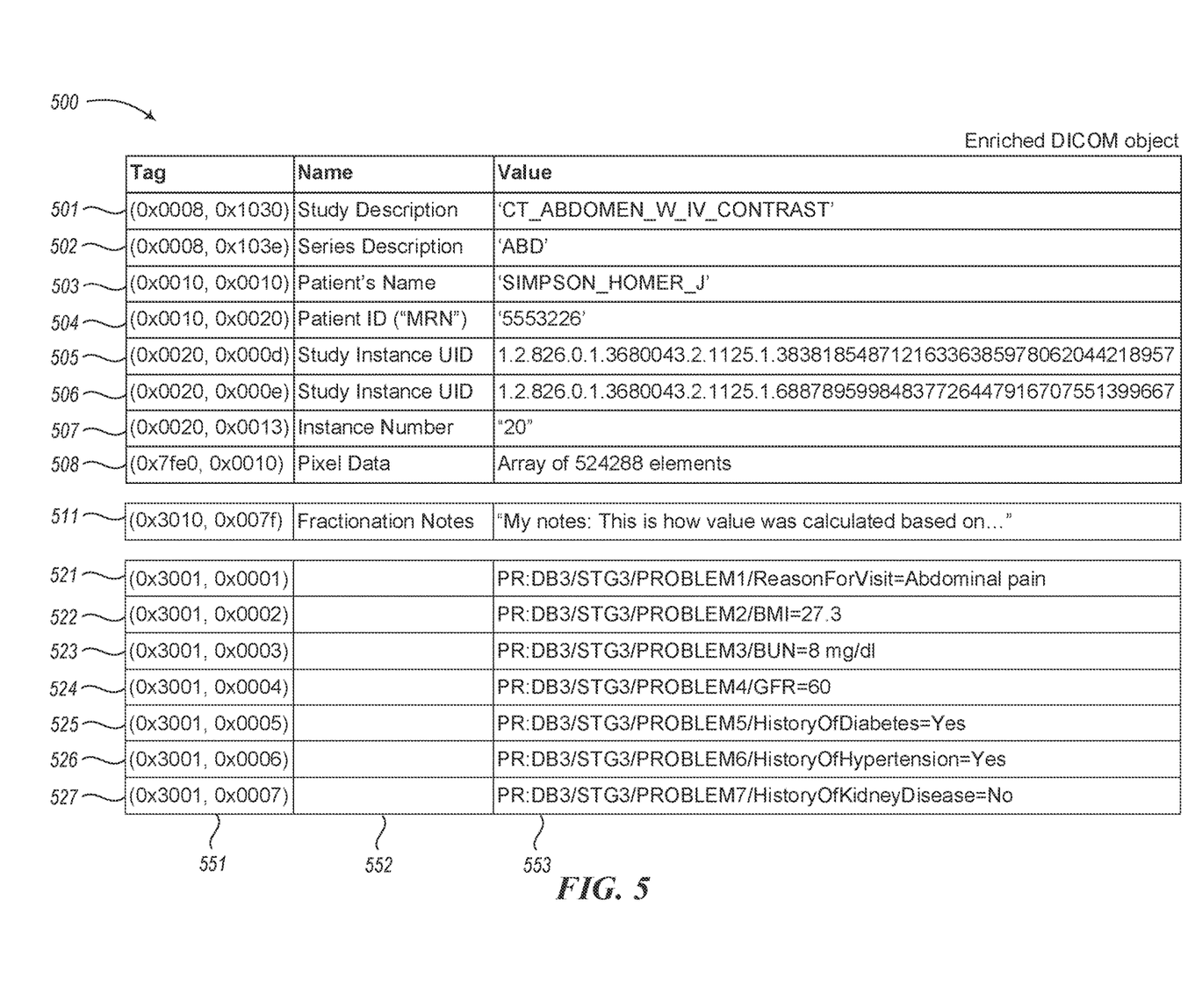
FIG. 5 is a table diagram showing sample contents of an enriched DICOM object corresponding to the DICOM object 300 shown in FIG. 3 and the configuration file shown in Table 1.

FIG. 5 is a table diagram showing sample contents of an enriched DICOM object corresponding to the DICOM object 300 shown in FIG. 3 and the configuration file shown in Table 1. The enriched DICOM object 500 is similar to DICOM object 300 shown in FIG. 3 in that each row corresponds to a different field of the enriched DICOM object. Rows 501-508 of the enriched DICOM object correspond to original rows 301-308 of the DICOM object 300. In some embodiments (not shown), in service of privacy objectives requirements, the facility omits to copy, or later deletes rows such as row 504 containing a Patient ID for the subject, and row 503, containing the Patient's Name. The rows further include row 511, corresponding to an inbuilt field specified by the DICOM standard that is populated as an additional field by the facility. In particular, row 511 corresponds to the FractionationNotes inbuilt field that is the subject of the first block of the configuration file occurring in lines 2-13. The value of this field is the one retrieved by the facility from the FractionationNotes column of the subject's row of the PROBLEM1 table in the STG1 schema of the DB1 database, as specified in rows 7-12 of the configuration file.

The enriched DICOM object further includes rows 521-527, each corresponding to an additional file that is stored in a custom tag. For example, row 521 for tag (0x3001, 0x0001) contains the value "Abdominal pain" retrieved by the facility from the ReasonForVisit column of the subject's row of the PROBLEM1 table in the STG3 schema of the DB3 database. The values in rows 522-527 are similarly retrieved by the facility in accordance with the remaining blocks of the configuration file.

Figure 6:
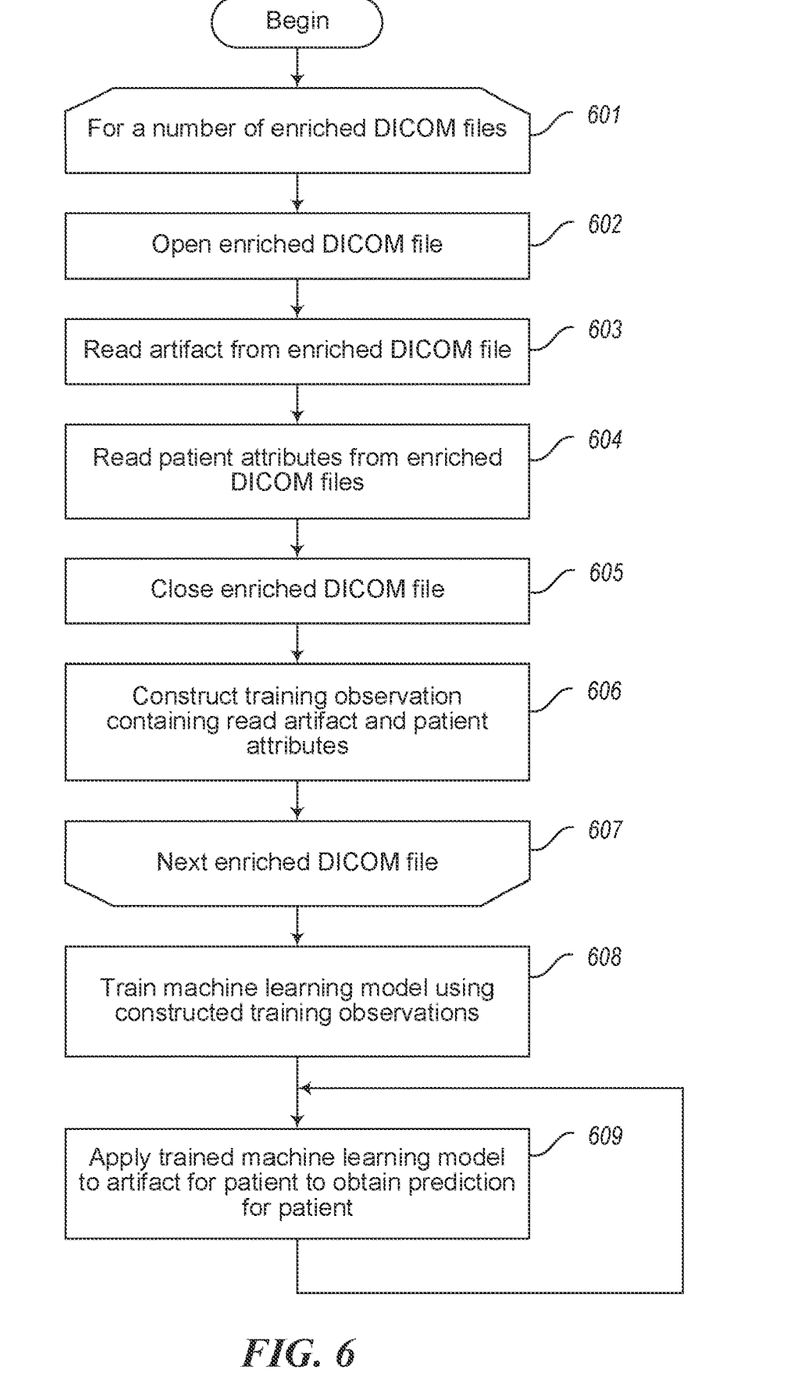
FIG. 6 is a flow diagram showing a process performed by the facility in order to train and apply a machine learning model using DICOM files enriched by the facility with additional medical information for the subjects of the medical imaging artifacts contained by those DICOM files.

FIG. 6 is a flow diagram showing a process performed by the facility in order to train and apply a machine learning model using DICOM files enriched by the facility with additional medical information for the subjects of the medical imaging artifacts contained by those DICOM files. The facility repeats rows 601-607 for each of a number of enriched DICOM files. In some embodiments, these are DICOM files retrieved by the facility from an EMR in accordance with a subject criteria query specified by a designer of the machine learning project or someone assisting them. In act 602, the facility opens the enriched DICOM file. In act 603, the facility reads the artifact from the enriched DICOM file. In the example of the enriched DICOM object 500, shown in FIG. 5, this artifact is the value stored in row 508. In the example of the enriched DICOM object 500, shown in FIG. 5, these patient attributes are the values of rows 511 and 521-527. In act 605, the facility closes the enriched DICOM file opened in act 602. In act 606, the facility constructs a training observation containing the artifact read in act 603 and the patient attributes read in act 604. In some embodiments, the facility constructs the training observation such that at least one of the patient attributes is identified as a dependent variable value, and the other patient attributes in the medical imaging artifact are identified as independent variable values. In act 607, if additional enriched DICOM files remain to be processed, then the facility continues in act 601, else the facility continues in act 608. In act 608, the facility trains a machine learning model using the training observations constructed in act 606. In various embodiments, the machine learning model that is trained is a deep learning network or other neural network, decision tree, random forest, support vector machine, naive Bayes classifier, or logistic regression, for example. In act 609, the facility applies the machine learning model trained in act 608 to a medical imaging artifact for a patient in order to obtain a prediction of the patient with respect to an appropriate value of the dependent variable(s) for the patient. In some embodiments, this application is to an enriched DICOM object created by the facility for the patient. After act 609, the facility continues in act 609 to apply the trained machine learning model to the next patient's medical imaging artifact.

The various embodiments described above can be combined to provide further embodiments. All of the U.S.

patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. One or more computer memories collectively storing an enrichment template data structure, comprising a plurality of entries, each entry corresponding to a different enrichment field for inclusion in an enriched DICOM object and comprising:
   extraction directions to extract medical information for the enrichment field from an identified source location in an electronic medical record corresponding to a subject from whom medical imaging information has been captured; and
   population directions to add to a copy of a starting DICOM object containing the medical imaging information captured from the subject the medical information extracted in accordance with the extraction directions in an identified target location in the DICOM object, the contents of the data structure being usable to generate from the starting DICOM object for the subject an enriched DICOM object.

2. The one or more computer memories of claim 1 wherein a first one of the plurality of entries contains population directions directing addition of the enrichment field to which the first entry corresponds in a target location that is a standard DICOM field, and wherein a first one of the plurality of entries contains population directions directing addition of the enrichment field to which the first entry corresponds in a target location that is a custom DICOM field.

3. The one or more computer memories of claim 1 wherein, for a first one of the plurality of entries, the extraction directions comprise a path that identifies a database column within a particular electronic medical record database.

4. One or more computer memories collectively having contents configured to cause a computing system to perform a method, the method comprising:
   receiving a plurality of enriched DICOM objects, each enriched DICOM object comprising:
      medical imaging information captured from a subject using a medical imaging device, and
      supplemental medical information about the subject extracted from an electronic medical record corresponding to the subject;
   for each of the plurality of enriched DICOM objects, establishing a training observation in which the medical imaging information of the enriched DICOM object and at least one unit of the supplemental medical information of the enriched DICOM object are employed as independent variables, and at least one unit of the supplemental medical information of the enriched DICOM is employed as a dependent variable; and
   training machine learning model with the established training observations.

5. The one or more computer memories of claim 4, wherein, for each of the plurality of enriched DICOM objects, establishing a training observation for the enriched DICOM object comprises accessing an enrichment template specifying fields of the enriched DICOM object in which particular units of the supplemental medical information are stored.

6. A method in a computing system, the method comprising:
   receiving a plurality of enriched DICOM objects, each enriched DICOM object comprising:
      medical imaging information captured from a subject using a medical imaging device, and
      supplemental medical information about the subject extracted from an electronic medical record corresponding to the subject;
   for each of the plurality of enriched DICOM objects, establishing a training observation in which the medical imaging information of the enriched DICOM object and at least one unit of the supplemental medical information of the enriched DICOM object are employed as independent variables, and at least one unit of the supplemental medical information of the enriched DICOM is employed as a dependent variable; and
   training machine learning model with the established training observations.

7. The method of claim 6, wherein, for each of the plurality of enriched DICOM objects, establishing a training observation for the enriched DICOM object comprises accessing an enrichment template specifying fields of the enriched DICOM object in which particular units of the supplemental medical information are stored.

8. A computing system, comprising:
   one or more processors; and
   one or more memories collectively having contents executable by the one or more processors to perform a method, the method comprising:
      receiving a plurality of enriched DICOM objects, each enriched DICOM object comprising:
         medical imaging information captured from a subject using a medical imaging device, and
         supplemental medical information about the subject extracted from an electronic medical record corresponding to the subject;
      for each of the plurality of enriched DICOM objects, establishing a training observation in which the medical imaging information of the enriched DICOM object and at least one unit of the supplemental medical information of the enriched DICOM object are employed as independent variables, and at least one unit of the supplemental medical information of the enriched DICOM is employed as a dependent variable; and
      training machine learning model with the established training observations.

9. The computing system of claim 8, wherein, for each of the plurality of enriched DICOM objects, establishing a training observation for the enriched DICOM object comprises accessing an enrichment template specifying fields of the enriched DICOM object in which particular units of the supplemental medical information are stored.

\* \* \* \* \*